(12) United States Patent
Meier et al.

(10) Patent No.: US 7,999,002 B2
(45) Date of Patent: *Aug. 16, 2011

(54) USE OF N-(DIBENZ(B,F)OXEPIN-10-YLMETHYL)-N-METHYL-N-PROP-2-YNYLAMINE (OMIGAPIL) OR A PHARMACEUTICALLY ACCEPTABLE ADDITION SALT THEREOF FOR THE PROPHYLAXIS AND/OR TREATMENT OF MUSCULAR DYSTROPHY

(75) Inventors: Thomas Meier, Basel (CH); Markus A. Ruegg, Riehen (CH)

(73) Assignee: Santhera Pharmaceuticals (Schweiz) AG, Liestal (CH)

( * ) Notice: Subject to any disclaimer, the term of this patent is extended or adjusted under 35 U.S.C. 154(b) by 612 days.

This patent is subject to a terminal disclaimer.

(21) Appl. No.: 12/063,268

(22) PCT Filed: Aug. 22, 2006

(86) PCT No.: PCT/EP2006/008237
§ 371 (c)(1),
(2), (4) Date: Feb. 8, 2008

(87) PCT Pub. No.: WO2007/022951
PCT Pub. Date: Mar. 1, 2007

(65) Prior Publication Data
US 2010/0160269 A1 Jun. 24, 2010

(30) Foreign Application Priority Data
Aug. 25, 2005 (EP) .................................. 05018530

(51) Int. Cl.
*A61K 31/335* (2006.01)

(52) U.S. Cl. ........ 514/450; 514/449; 514/183; 549/354; 549/346; 549/200

(58) Field of Classification Search ........................ None
See application file for complete search history.

(56) References Cited

U.S. PATENT DOCUMENTS

| | | | | |
|---|---|---|---|---|
| 5,780,244 A * | 7/1998 | Engvall et al. | ............. | 435/7.21 |
| 5,780,500 A * | 7/1998 | Betschart et al. | ............. | 514/450 |
| 5,780,501 A * | 7/1998 | Betschart et al. | ............. | 514/450 |
| 5,863,743 A * | 1/1999 | Campbell et al. | ............. | 435/7.21 |
| 7,078,379 B2 * | 7/2006 | Ruegg | ............. | 514/2 |
| 2009/0176867 A1 * | 7/2009 | Meier | ............. | 514/450 |

FOREIGN PATENT DOCUMENTS

| | | |
|---|---|---|
| CA | 2168937 | 2/1996 |
| EP | 0 726 265 A1 | 8/1996 |
| WO | WO 00/49011 | 8/2000 |

OTHER PUBLICATIONS

McGowan et al., "Laminins and Human Disease," Microscopy Research and Technique 51, 262-79 (2000).*
Waldmeier et al., "GCP 3466 protects dopaminergic neurons in lesion models of Parkinson's disease," Naunyn-Schmiedeber's Arch. Pharmacol. 362, 526-37 (2000).*
Urtizberea, "Therapies in Muscular Dystrophy: Current Concepts and Future Prospects," Eur. Neurol. 43, 127-32 (2000).*
"The muscular dystrophies," by Emery, Lancet 359, 687-95 (2002).*
Definition of "Prophylaxis," Stedman's Medical Dictionary, 26th Ed., Williams & Wilkins (Baltimore), p. 1439 (1995).*
"Glyceraldehyde-3-phosphate Dehydrogenase, the Putative Target of the Antiapoptotic Compounds CGP 3466 and R-(-)-Deprenyl" by Kragten et al., J. Biol. Chem. 273, 5821-28 (1998).*
"Merosin-deficient Congenital Muscular Dystrophy: Partial Genetic Correction in Two Mouse Models" by Kuang et al., J. Clin. Invest. 102, 844-52 (1998).*
International Search Report for PCT/EP2006/008237 dated Nov. 23, 2006.
Andringa et al., "TCH346 prevents motor symptoms and loss of striatal FDOPA uptake in bilaterally MPTP-treated primates," Neurobiology of Disease, vol. 14, 2003, pp. 205-217.

* cited by examiner

*Primary Examiner* — Anish Gupta
*Assistant Examiner* — Theodore R West
(74) *Attorney, Agent, or Firm* — Kilyk & Bowersox, P.L.L.C.

(57) ABSTRACT

The invention relates to the use of a compound of the formula (I)

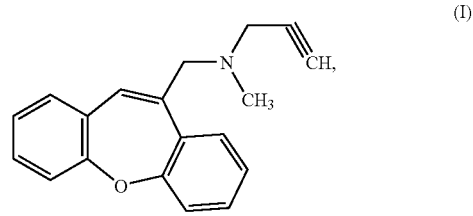

or a pharmaceutically acceptable addition salt thereof for the preparation of a medicament for the prophylaxis and/or treatment of muscular dystrophy.

9 Claims, 6 Drawing Sheets

USE OF N-(DIBENZ(B,F)OXEPIN-10-YLMETHYL)-N-METHYL-N-PROP-2-YNYLAMINE (OMIGAPIL) OR A PHARMACEUTICALLY ACCEPTABLE ADDITION SALT THEREOF FOR THE PROPHYLAXIS AND/OR TREATMENT OF MUSCULAR DYSTROPHY

This application is a National Stage Application of PCT/EP2006/008237, filed Aug. 22, 2006, which claims priority from European Patent Application No. 05018530.5, filed Aug. 25, 2005.

The present invention relates to the use of N-(dibenz(b,f)oxepin-10-ylmethyl)-N-methyl-N-prop-2-ynylamine or a pharmaceutically acceptable addition salt thereof for the prophylaxis and/or treatment of muscular dystrophy, preferably congenital muscular dystrophies, in particular congenital muscular dystrophy resulting from laminin-α2 deficiency.

Congenital muscular dystrophy (CMD) is a heterogeneous group of muscle disorders characterized by muscle wasting, muscle fiber necrosis and fibrosis. The feature that makes it distinct from other muscular dystrophies, in particular to limb-girdle muscular dystrophies, is the early onset of symptoms at birth or within the first 6 months of life. CMDs are mostly autosomal recessive diseases. In addition to the involvement of muscle, some CMDs also show cerebral malformations and are often associated with mental retardation. The recent progress in deciphering the molecular origin of this disease implies dysregulation of α-dystroglycan as one of the key feature in CMD. Today, CMD is subgrouped into ten distinct diseases based on their genetic origin. Generally, the prevalence of CMD is low (approx. $1-2.5 \times 10^{-5}$).

Merosin-deficient CMD which was recently renamed MDC1A, is one of the main subgroups. Its prevalence varies greatly between countries. For example, approximately half of all the CMD patients in Europe suffer from MDC1A, while only about 6% of CMD patients belong to this subgroup in Japan.

MDC1A (MIM 156 225) is caused by mutations in the gene encoding the laminin α2 chain (previously called merosin) located on human chromosome 6q2 (Helbling-Leclerc A, et al. (1995)—Mutations in the laminin-α2-chain gene (LAMA2) cause merosin-deficient congenital muscular dystrophy. Nat Genet 11: 216-218).

Pharmacological intervention for the treatment of MDC1A is limited to supportive treatment, in particular anti-infectives to overcome frequently observed infections of the respiratory tract. Important aspects of disease management include orthopedic surgery of scoliosis as well as supplementary nutrition to avoid malnutrition. Special guidelines about ventilatory support in congenital muscular dystrophies were published (Wallgren-Pettersson C. et al. (2004)—117th ENMC workshop: ventilatory support in congenital neuromuscular dystrophies, congenital myotonic dystrophy and SMA (II). *Neuromusc. Disord.* 14:56-69).

Innovative treatment options may stem from recent findings in laminin-α2 deficient mice that overexpressed a miniaturized and tailored version of the extracellular matrix molecule agrin. It was demonstrated that this "mini-agrin" functionally substitutes for the missing linkage between the cell-surface receptor alpha dystroglycan and the misexpressed laminin network. Expression of this artificial and non-homologues "mini agrin" significantly prolonged the life span of laminin α2-deficient mice, improved the motor performance and normalized the muscle histology (Moll J. et al. (2001). An agrin minigene rescues dystrophic symptoms in a mouse model for congenital muscular dystrophy, *Nature* 413: 302-307; Qiao C. et al. (2005)—Amelioration of laminin α2-deficient congenital muscular dystrophy by somatic gene transfer of miniagrin, *Proc. Natl. Aced Sci* USA 102:11999-12004). However, these gene therapy approaches rely on somatic gene therapy which still is not a routine procedure in human patients.

BRIEF DESCRIPTION OF THE DRAWINGS

FIG. 5 (D) is a graph showing the kyphosis score for a 9 vehicle- and a 7 omigapil-treated animal.

Figure 1:
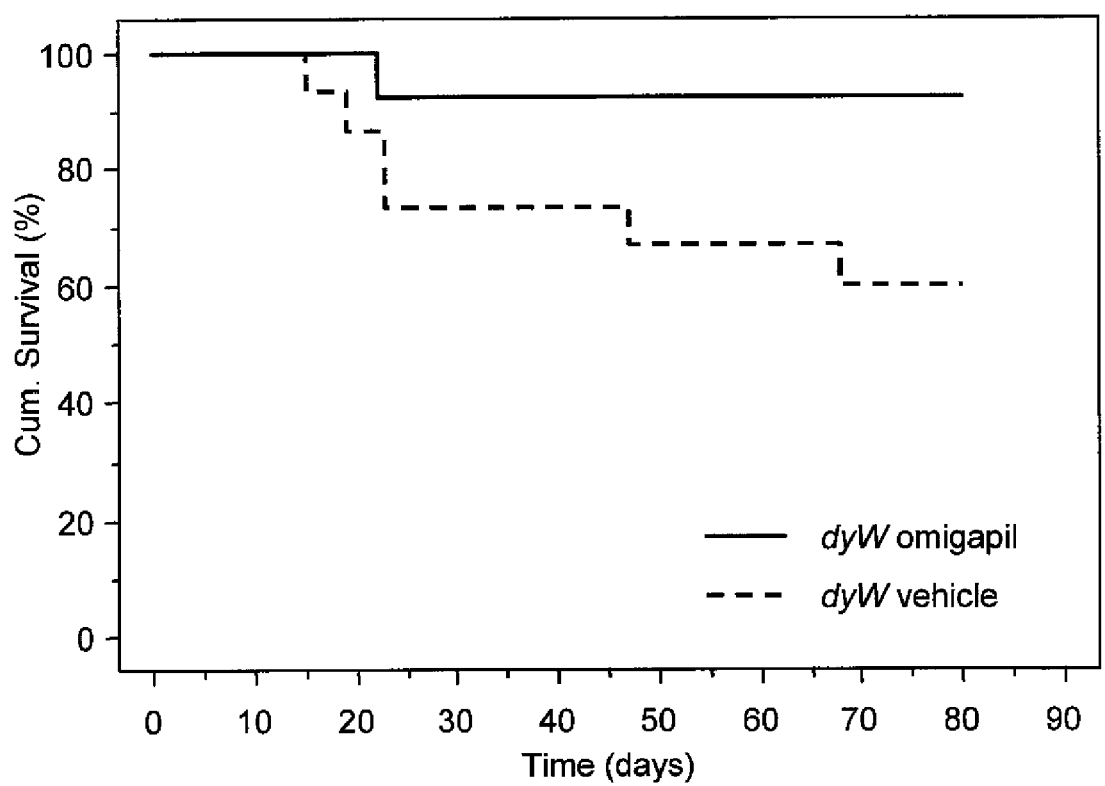
FIG. 1 is a graph showing a Kaplan-Meier cumulative survival plot for life-span (days).

The problem underlying the present invention is to provide a compound which is suitable for the prophylaxis and/or treatment of muscular dystrophy, especially its devastating complications resulting from laminin-α2 deficiency.

This problem is solved by the use of a compound of formula (I)

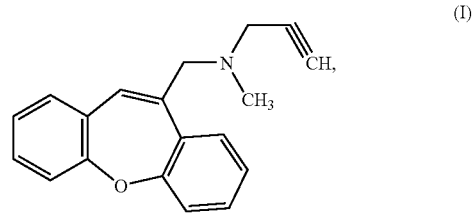

or a pharmaceutically acceptable addition salt thereof for the preparation of a medicament for the prophylaxis and/or treatment of muscular dystrophy.

The compound of formula (I) or an addition salt thereof is preferably used for the prophylaxis and/or treatment of congenital muscular dystrophies, in particular Congenital Muscular Dystrophy 1A (MDC1A) resulting from partial or complete loss of laminin-α2.

The compound of formula (I) is N-(dibenz(b,f)oxepin-10-ylmethyl)-N-methyl-N-prop-2-ynylamine. The compound of formula (I) or salts thereof has been proposed and investigated as potential treatment option for various neurodegenerative diseases in which apoptotic cytolysis plays a role. Such neurodegenerative diseases include cerebral ischemia, Alzheimer's disease, Huntington's disease and Parkinson's disease, amyotrophic lateral sclerosis, multiple sclerosis, types of glaucoma, retina degeneration, as well as general or diabetic peripheral neuropathy. The use of the compound of formula (I) or salts thereof for the treatment of these diseases as well as processes for the preparation of omigapil are disclosed in WO 97/45422, EP-A-0726265, WO 2004/066993 and WO 2005/044255. It has furthermore been reported that the compound of formula (I) binds to glyceraldehyde-3-phosphate dehydrogenase (GAPDH) and exerts antiapoptotic effects (Kragten E et al. (1998)—Glyceraldehyde-3-phosphate dehydrogenase, the putative target of the antiapoptotic compounds CGP 3466 and R(−)deprenyl. *J. Biol. Chem.* 273: 5821-5828).

The pharmaceutically acceptable addition salt of the compound of formula (I) is preferably a salt of a mineral acid or an organic carboxylic acid. In a more preferred embodiment the organic carboxylic acid is an optionally hydroxylated ($C_{1-7}$) alkanoic acid, an optionally hydroxylated, aminated and/or oxo-substituted ($C_{2-7}$)alkane-dicarboxylic acid, an optionally hydroxylated and/or oxo-substituted ($C_{3-7}$)alkane-tricarboxylic acid, an optionally hydroxylated and/or oxo-substituted ($C_{4-7}$)alkene-dicarboxylic acid, optionally hydroxylated and/or oxo-substituted ($C_{4-7}$)alkine-dicarboxylic acid, an aliphatic or aromatic sulfonic acid, or an aliphatic or aromatic N-substituted sulfamic acid.

In a further preferred embodiment the addition salt of the compound of formula (I) contains an anion selected from the group consisting of chloride, perchlorate, bromide, iodide, nitrate, phosphate, acid phosphate, sulfate, methanesulfonate, ethanesulfonate, benzenesulfonate, p-toluenesulfonate, naphthalene-2-sulfonate, bisulfate, N-cyclohexylsulfamate, carbonate, formate, acetate, propionate, pivalate, glycolate, lactate, gluconate, glucuronate, ascorbate, pantothenate, oxalate, malonate, succinate, glutamate, aspartate, tartrate, bitartrate, malate, citrate, aconate, fumarate, maleate, itaconate, acetylene dicarboxylate, benzoate, salicylate, phthalate, phenylacetate, mandelate, cinnamate, p-hydroxybenzoate, 2,5-dihydroxy-benzoate, p-methoxybenzoate, hydroxy naphthoate, nicotinate, isonicotinate and saccharate.

In another preferred embodiment the addition salt of the compound of formula (I) contains a cation selected from the group consisting of $H^+$, $Na^+$ and $K^+$.

The maleate of the compound of formula (I), i.e. N-(dibenz (b,f)oxepin-10-ylmethyl)-N-methyl-N-prop-2-ynylammonium maleate, is particularly preferred. This compound is also known as omigapil, CGP 3466 or TCH346.

The present invention is also directed to a method for therapeutic and/or prophylactic treatment of a mammal requiring treatment, by administration of an effective amount of a compound of formula (I) or a pharmaceutically acceptable addition salt thereof for the prophylaxis and/or treatment of muscular dystrophy, preferably congenital muscular dystrophies, in particular Congenital Muscular Dystrophy 1A (MDC1A) resulting from partial or complete loss of laminin-α2.

It is preferred that the compound of formula (I) or a pharmaceutically acceptable addition salt thereof is used together with a second therapeutic agent. More preferably the second therapeutic agent is any medicament used in MDC1A patients to treat muscle weakness resulting from laminin-α2 deficiency. Even more preferably, the second therapeutic agent is selected from the group consisting of glucocorticosteroids, calpain inhibitors, inhibitors of the proteasome and antiinfectives. The glucocorticosteroid is for example 6a-methylprednisolone-21 sodium succinate (Solumedrol®) or deflazacort (Calcort®). Suitable calpain inhibitors are for example disclosed in WO 2004/078908. The inhibitor of the proteasome is for example bortezomib (Velcade®). The antiinfectives are suitably selected from anti-infectives which are routinely used for the treatment of respiratory infections in MDC1A patients.

The compound of formula (I) or a pharmaceutically acceptable addition salt thereof and the second therapeutic agent can be used simultaneously, separately or sequentially in order to prevent or treat the disease symptoms. The two therapeutic agents may be provided in a single dosage form or a separate formulation, each formulation containing at least one of the two therapeutic agents.

The compound of formula (I) or a pharmaceutically acceptable addition salt thereof is preferably used for treating or preventing weakness and loss of skeletal muscle tissue associated with congenital muscular dystrophy resulting from laminin-α2 deficiency, in particular MDC1A. Specifically, the invention relates to the use of a compound of formula (I) or a pharmaceutically acceptable addition salt thereof for treating congenital muscular dystrophy type MDC1A by administering an effective amount of the compound of formula (I) or a pharmaceutically acceptable addition salt thereof, preferably N-(dibenzo[b,f]oxepin-10-ylmethyl)-N-methyl-N-prop-2-inyl-ammonium salts and in particular N-(dibenzo[b,f]oxepin-10-ylmethyl)-N-methyl-N-prop-2-inyl-ammonium maleate.

The effective dosage of the active ingredient employed may vary depending on the particular compounds employed, the mode of administration, the condition being treated and the severity of the condition being treated. Such dosage may be ascertained readily by a person skilled in the art. In humans the compound of formula (I) or a pharmaceutically acceptable addition salt thereof is preferably administered in a dosage range of 0.01 mg/day to 80 mg/day, more preferably in a dosage range of 0.05 mg/day to 40 mg/day and most preferred in a dosage range of 0.1 mg/day to 20 mg/day.

Further, the compound of formula (I) or a pharmaceutically acceptable addition salt thereof is preferably administered at least once a day, preferably for at least 3 months, more preferably for at least 6 months, most preferably for 6 months to 12 months to observe the initial amelioration of the disease symptoms (as for example but not exclusively amelioration of muscle weakness, respiratory problems) associated with MDC1A resulting from laminin-α2 deficiency. For maintenance of the therapeutic effect prolonged treatment is recommended; the preferred treatment is lifelong.

Any suitable route of administration may be employed for providing a mammal, especially a human, with an effective dosage of the compound of formula (I) or a pharmaceutically acceptable addition salt thereof. The modes of administration include rectal, topical, ocular, pulmonary, oral, intraperitoneal (i.p.), intravenous (i.v.), intramuscular (i.m.), intracavernous (i.c.), parenteral, intranasal and transdermal. Preferred modes of administration are oral, intraperitoneal, intravenous, intramuscular, intracavernous, parenteral, intranasal and transdermal, whereas the oral administration is the most preferred mode of administration.

The compound of formula (I) or a pharmaceutically acceptable addition salt thereof is preferably formulated into a dosage form prior to administration. The dosage forms include, e.g., tablets, pills, granules, powders, lozenges, sachets, cachets, elixirs, aqueous and oil-based suspensions, emulsions, dispersions, solutions such as sterile injectable solutions, syrups, aerosols (as a solid or in a liquid medium), capsules such as soft and hard gelatin capsules, suppositories, sterile packaged powders, troches, creams, ointments and aerosols. Tablets are most preferred.

For oral application suitable preparations are in the form of tablets, sugar-coated pills, capsules, granular powders, drops, juices and syrups, while for parenteral, topical and inhalative application suitable forms are solutions, suspensions, easily reconstitutable dry preparations as well as sprays.

Accordingly, the compound of formula (I) or a pharmaceutically acceptable addition salt thereof may be combined with any suitable pharmaceutical carrier. The pharmaceutical preparations for use in accordance with the present invention may be prepared by normal procedures using well-known and readily available ingredients. Such ingredients can be excipients, fillers, solvents, diluents, dyes and/or binders.

In making the formulations, the compound of formula (I) or a pharmaceutically acceptable addition salt thereof is usually mixed with a carrier, or diluted by a carrier, or enclosed with a carrier, which may be in the form of a capsule, cachet, paper or other container.

When the carrier serves as a diluent, it may be a solid, semi-solid, or liquid material, which acts as a vehicle, excipient or medium for the active ingredient.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil.

The formulations can additionally include lubricating agents, wetting agents, emulsifying and suspending agents, preserving agents, sweetening agents and/or flavoring agents.

The choice of auxiliary substances as well as the amounts thereof to be used depends on whether the medicinal drug is to be administered orally, intravenously, intraperitoneally, intradermally, intramuscularly, intranasally, buccally or topically.

The compound of formula (I) or a pharmaceutically acceptable addition salt thereof may be formulated so as to provide quick, sustained or delayed release of the active ingredient after administration to the patient. To this end, the compound of formula (I) or a pharmaceutically acceptable addition salt thereof can for example be administered in a sustained-release substance, in dissolved form or in a plaster, optionally with the addition of agents promoting penetration of the skin, and are suitable as percutaneous application preparations. Forms of preparations that can be used orally or percutaneously may produce a delayed release of the compounds.

The compound of formula (I) or a pharmaceutically acceptable addition salt thereof is toxically safe which means that it can be used as a pharmaceutical active agent in a medicament.

The following examples further illustrate the invention.
Animal Models of MDC1A

Almost fifty years ago, the dystrophia muscularis (dy/dy) mouse was identified in the Jackson Laboratories (Michelson A M, Russell E S, Harman P J. (1955)—Dystrophia muscularis: a hereditary primary myopathy in the house mouse, *Proc Natl Acad Sci USA,* 41:1079-1084). This and another spontaneous mutant, called $dy^{2J}/dy^{2J}$ (Meier H, Southard JL. (1970)—Muscular dystrophy in the mouse caused by an allele at the dy-locus, *Life Sci.* 9:137-144; Xu H. et al. (1994)—Murine muscular dystrophy caused by a mutation in the laminin-α2 (Lama2) gene, *Nature Genetics* 8:296-302), are both hypomorphs for the laminin α2 chain (Guo L T, Zhang X U, Kuang W, et al. (2003)—Laminin-α2 deficiency and muscular dystrophy; genotype-phenotype correlation in mutant mice, *Neuromuscul. Disord.* 13(3):207-215). In addition, two mice models, called $dy^W/dy^W$ (Kuang W, Xu H, Vachon P H, et al. (1998)—Merosin-deficient congenital muscular dystrophy. Partial genetic correction in two mouse models, *J. Clin. Invest.* 102(4):844-852) and $dy^{3K}/dy^{3K}$ (Miyagoe Y, Hanaoka K, Nonaka I, et al. (1997)—Laminin-α2 chain-null mutant mice by targeted disruption of the Lama2 gene: a new model of merosin (laminin 2)-deficient congenital muscular dystrophy, *FEBS Lett.* 415(1):33-39) are based on homologous recombination.

The phenotype of laminin-α2—deficient mice closely resembles the human pathology. For example, mice die early (i.e. 3-16 weeks) after birth, they grow at a much slower rate than wild-type littermates and all mice develop scoliosis. Three weeks after birth, muscle strength is significantly lower compared to wild-type mice. The histology of affected muscles is very similar to that of human patients and is characterized by great variation in fiber size, extensive fibrosis, infiltration of adipose tissue, and high levels of creatine kinase in the blood. In addition, the hindlegs of laminin-α2-deficient mice become paralyzed after a few weeks and abnormal myelination can be observed in the central nervous system. Thus, these mice are a well recognized and widely used model for discovering the potential molecular mechanisms underlying the disease.

EXAMPLE 1

The effect of N-(dibenz(b,f)oxepin-10-ylmethyl)-N-methyl-N-prop-2-ynylammonium maleate (omigapil) on the survival rate was tested in a mouse model for MDC1A deficient in laminin-α2 expression. Starting at day fifteen, homozygous $dy^W/dy^W$ mice were treated with omigapil. Their survival rate was compared to homozygous $dy^W/dy^W$ mice treated with vehicle only. For this, omigapil was dissolved in 0.5% w/v ethanol to a final concentration of 20 μg/ml. The treatment regime was as follows: omigapil (20 μg/ml in 0.5% ethanol) was applied to 3 week old $dy^W/dy^W$-mice by intraperitoneal (i.p.) injection once per day; from the 4th week of age onwards mice received the same concentration of omigapil once per day by gavage feeding instead of i.p. application. The final dose of omigapil given to $dy^W/dy^W$-mice at all times was 0.1 mg/kg body weight, once daily following the guidance as described elsewhere (Sagot Y. et al. (2000)—An orally active anti-apoptotic molecule (CGP 3466B) preserves mitochondria and enhances survival in an animal model of motoneuron disease. *Br. J. Pharmacol.* 131: 721-728). Control mice received the equivalent amount of vehicle only.

Surprisingly it was found that omigapil significantly prevented from early death in $dy^W/dy^W$ mice. As demonstrated in FIG. 1, 6 out of 15 (=40%) vehicle-treated $dy^W/dy^W$ mice died within the first 80 days of age while in the omigapil-treated group only 1 out of 13 (=8%) animals died at this age. It can be concluded from this data that omigapil prevents from early morbidity and mortality in an animal model for muscular dystrophy caused by laminin α2-deficiency.

FIG. 1 shows a Kaplan-Meier cumulative survival plot for life-span (days). Newborn $dy^W/dy^W$ mice were genotyped according to the method described in (Kuang, W., H. Xu, et al. (1998)—"Merosin-deficient congenital muscular dystrophy. Partial genetic correction in two mouse models," J Clin Invest 102(4): 844-52) and randomly assigned to the vehicle or omigapil group. In total 15 and 13 animals were included into the vehicle and the omigapil group, respectively.

EXAMPLE 2

Example 2 describes the therapeutically relevant effect of N-(dibenz(b,f)oxepin-10-ylmethyl)-N-methyl-N-prop-2-ynylammonium maleate (omigapil) on the body weight gain in a mouse model for MDC1A deficient in laminin-α2 expression. Starting at day fifteen, homozygous $dy^W/dy^W$ mice were treated with omigapil. Their individual body weights were assessed daily and compared to homozygous $dy^W/dy^W$ mice treated with vehicle only (control group). For this, omigapil was given to dy$^W$/dy$^W$-mice at doses of 0.1 or 1 mg/kg body weight, respectively. The treatment regime was as described in example 1.

Surprisingly it was found that omigapil considerably increased the body weight gain in dy$^W$/dy$^W$-mice. As demonstrated in FIG. 2, maximally 11% of the vehicle-treated dy$^W$/dy$^W$ mice reached a body weight above 12 grams within the first 11 weeks of age while 25% and 43% reached a body weight above this threshold in the 0.1 and 1 mg/kg omigapil-treated groups, respectively. It can be concluded from this data that omigapil prevents from reduced body weight in an animal model for muscular dystrophy caused by laminin α2-deficiency.

Figure 2:
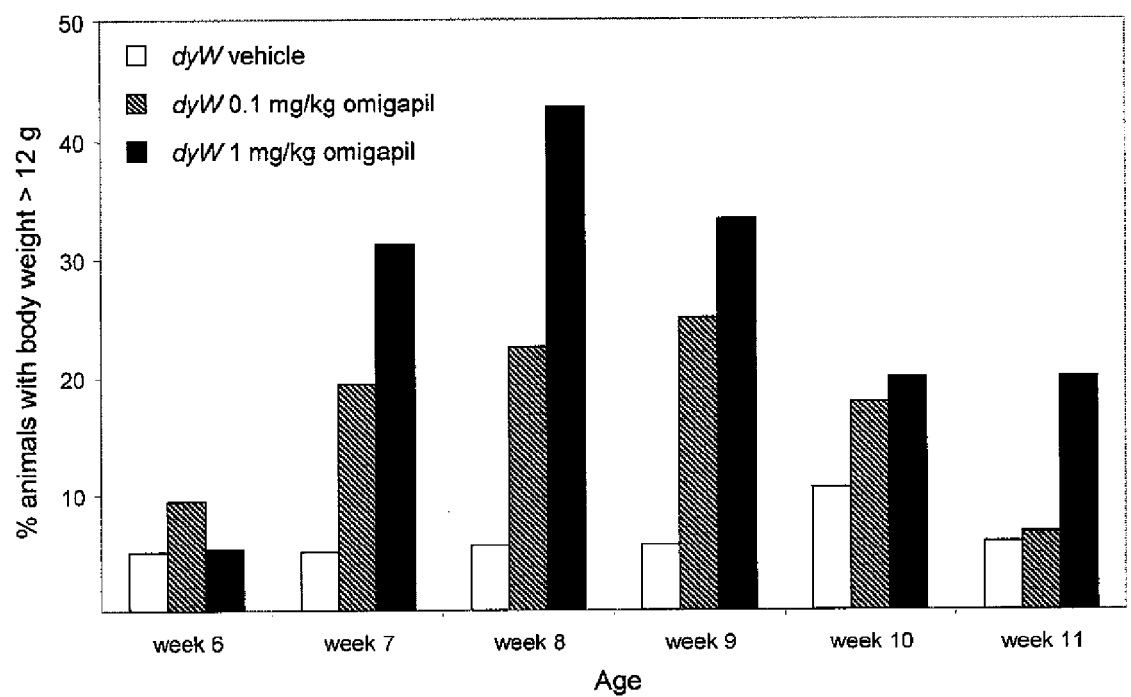
FIG. 2 is a bar graph showing, on a weekly basis, the percentage of animals between 6 and 11 weeks of age with a body weight above a threshold of 12 grams.

FIG. 2 shows on a weekly basis the percentage of animals between 6 and 11 weeks of age with a body weight above a threshold of 12 grams. Newborn dy$^W$/dy$^W$ mice were genotyped and randomly assigned to the vehicle or the 0.1 and 1 mg/kg omigapil groups. The individual body weights were assessed daily and the mean body weight were calculated every week. The percentage of mice above an average body weight of twelve grams is shown grouped according to age (between 6 and 11 weeks) for each treatment group. In total 27, 34 and 25 animals were included into the vehicle, the 0.1 and the 1 mg/kg omigapil group, respectively.

EXAMPLE 3

The effect of N-(dibenz(b,f)oxepin-10-ylmethyl)-N-methyl-N-prop-2-ynylammonium maleate (omigapil) on skeletal muscle apoptosis was tested in a mouse model for MDC1A deficient in laminin-α2 expression. Starting at day fifteen, homozygous dy$^W$/dy$^W$ mice were treated with omigapil. The number of apoptotic myonuclei were analyzed and compared to the number of apoptotic myonuclei determined in homozygous dy$^W$/dy$^W$ mice treated with vehicle only and to the number of apoptotic myonuclei determined in untreated wild-type mice. For this, omigapil was given to dy$^W$/dy$^W$-mice at a dose of 0.1 mg/kg body weight according to the treatment regime described in example 1.

Surprisingly it was found that omigapil considerably reduced the number of apoptotic myonuclei in the Triceps muscle in dy$^W$/dy$^W$-mice. As demonstrated in FIG. 3, 1.1% of the myofibers in the Triceps muscle of the vehicle-treated dy$^W$/dy$^W$ mice had apoptotic myonuclei at 6 weeks of age while only 0.7% apoptotic myofibres were detected in the omigapil-treated group. It can be concluded from this 35% reduction in apoptotic myofibres that omigapil prevents from increased apoptotic myofiber death in an animal model for muscular dystrophy caused by laminin α2-deficiency.

Figure 3:
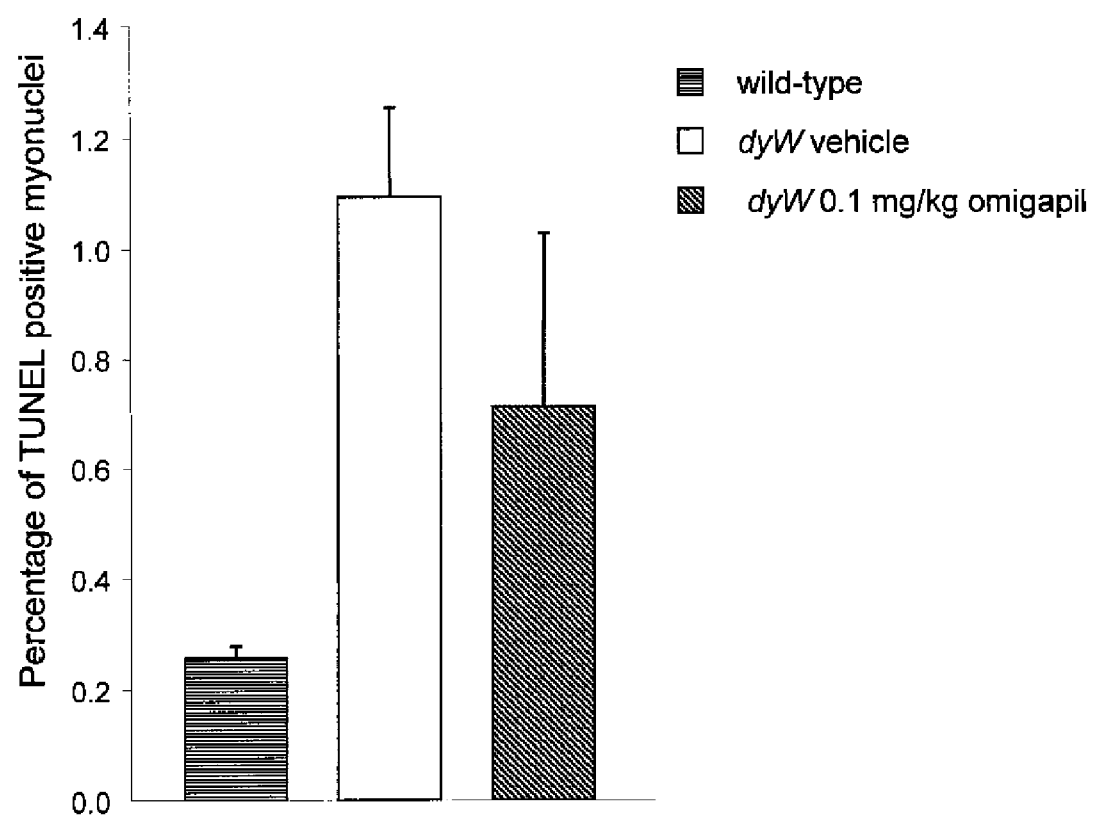
FIG. 3 is a bar graph showing the percentage of apoptotic myofibres in the Triceps muscle of 6-week-old mice.

FIG. 3 shows the percentage apoptotic myofibres in the Triceps muscle of 6-weeks-old dy$^W$/dy$^W$ mice. Newborn dy$^W$/dy$^W$ mice were genotyped and randomly assigned to the vehicle or omigapil group. The apoptotic myonuclei in the Triceps foreleg muscle were determined by counting muscle fibers positively stained for Terminal dUTP nick end labeling (TUNEL). For each muscle, all muscle fibers of one cross section were included into the analysis. The relative number of apoptotic myofibres was calculated by dividing the number of TUNEL positive myonuclei by the total number of myofibres. 7 animals were analyzed per treatment group. 1.1% of the myofibers in the Triceps muscle of the vehicle-treated dy$^W$/dy$^W$ mice had apoptotic myonuclei at 6 weeks of age while only 0.7% apoptotic myofibres were detected in the omigapil-treated group. For comparison, the number of TUNEL positive muscle fibers in untreated wild-type animals is shown as well.

EXAMPLE 4

The effect of N-(dibenz(b,f)oxepin-10-ylmethyl)-N-methyl-N-prop-2-ynylammonium maleate (omigapil) on muscle fiber size distribution was tested in a mouse model for MDC1A deficient in laminin-α2 expression. Muscle fiber diameters were analyzed in Triceps muscle of 6 weeks old dy$^W$/dy$^W$ mice treated with 0.1 mg/kg body weight omigapil or with vehicle only. The treatment regime was as described in example 1.

Surprisingly it was found that omigapil significantly increased the relative number of large diameter muscle fibers in the Triceps muscle in dy$^W$/dy$^W$-mice. As demonstrated in FIG. 4, 8% of the myofibers in the Triceps muscle of the vehicle-treated dy$^W$/dy$^W$ mice had muscle fiber diameters above 50 micrometers at 6 weeks of age while 15% of myofibres in the omigapil-treated group had muscle fiber diameters above 50 micrometers. It can be concluded from this increase in large diameter myofibers that omigapil improves muscle histology in an animal model for muscular dystrophy caused by laminin α2-deficiency.

Figure 4:
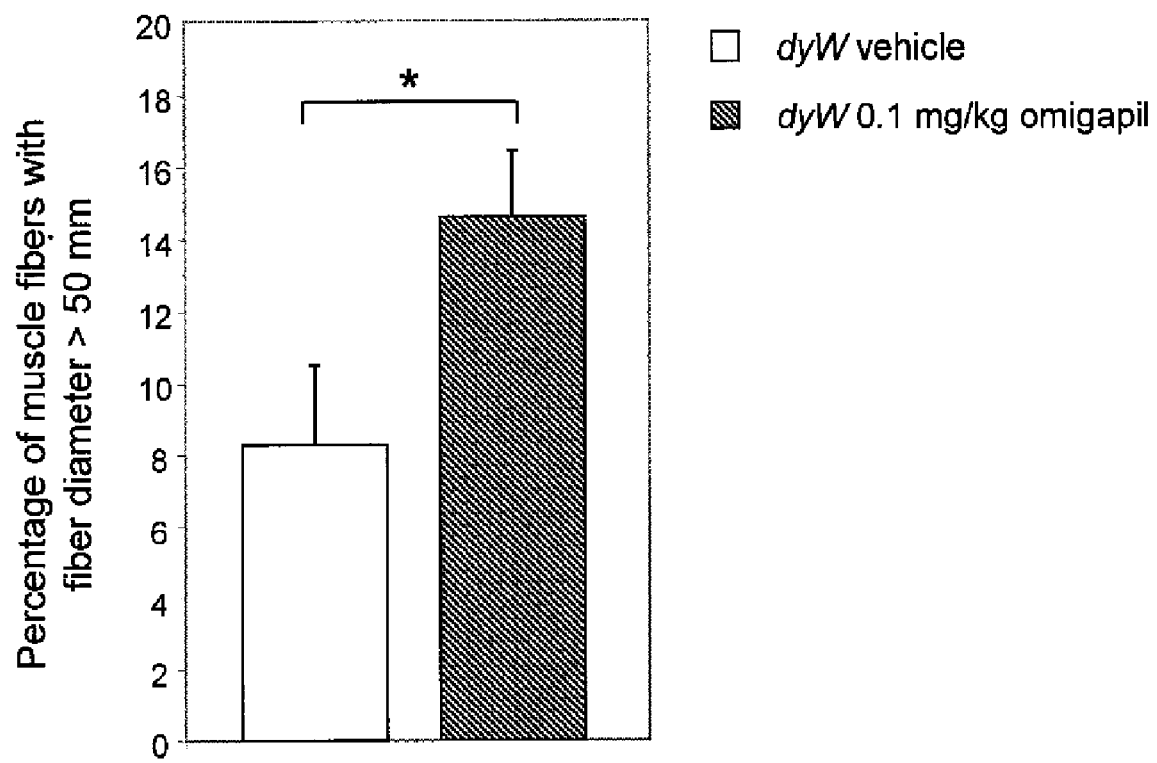
FIG. 4 is a bar graph showing the percentage of large diameter muscle fibers in the Triceps muscle of 6-week-old mice.

FIG. 4 shows the percentage of large diameter muscle fibers in the Triceps muscle of 6-weeks-old dy$^W$/dy$^W$ mice. Newborn dy$^W$/dy$^W$ mice were genotyped and randomly assigned to the vehicle or omigapil group. The myofiber diameters were measured following methods known to the skilled artist (Briguet, A., Courdier-Fruh, I., Foster, M., Meier, T., Magyar, J. P. (2004)—"Histological parameters for the quantitative assessment of muscular dystrophy in the mdx-mouse", Neuromuscul Disord 14(10): 675-82). For each muscle all muscle fibers of one cross section were included into the analysis. 7 animals were analyzed per treatment group. 8% of the myofibers in the Triceps muscle of the vehicle-treated dy$^W$/dy$^W$ mice had muscle diameters above 50 micrometers at 6 weeks of age while 15% of myofibres in the omigapil-treated group fulfilled this criteria. Asterisk: p-value<0.05.

EXAMPLE 5

The beneficial and therapeutically relevant effect of N-(dibenz(b,f)oxepin-10-ylmethyl)-N-methyl-N-prop-2-ynylammonium maleate (omigapil) on the skeletal deformation (i.e. kyphosis) was tested in a mouse model for MDC1A deficient in laminin-α2 expression. For this, homozygous dy$^W$/dy$^W$ mice were treated with omigapil (at a dose of 1 mg/kg body weight) and their kyphosis was scored at 11 weeks of age by visual inspection and X-ray analysis and compared to the extent of kyphosis seen in homozygous dy$^W$/dy$^W$ mice treated with vehicle only and untreated wild-type mice. The treatment regime was as described in example 1.

Surprisingly it was found that omigapil considerably decreased the kyphosis in dy$^W$/dy$^W$-mice. As demonstrated by the example in FIG. 5, the spine of the vehicle-treated dy$^W$/dy$^W$ mice spanned an angle of 66° at 11 weeks of age indicating severe kyphosis while the spine of the omigapil-treated dy$^W$/dy$^W$ mice spanned an angle of 89° clearly indicating less severe skeletal deformation. By comparison to the situation in untreated wildtype mice it can be concluded that treatment with omigapil can significantly ameliorate the spinal deformation (i.e. reduction in the spinal kyphosis) in an animal model for muscular dystrophy caused by laminin α2-deficiency.

Figure 5:
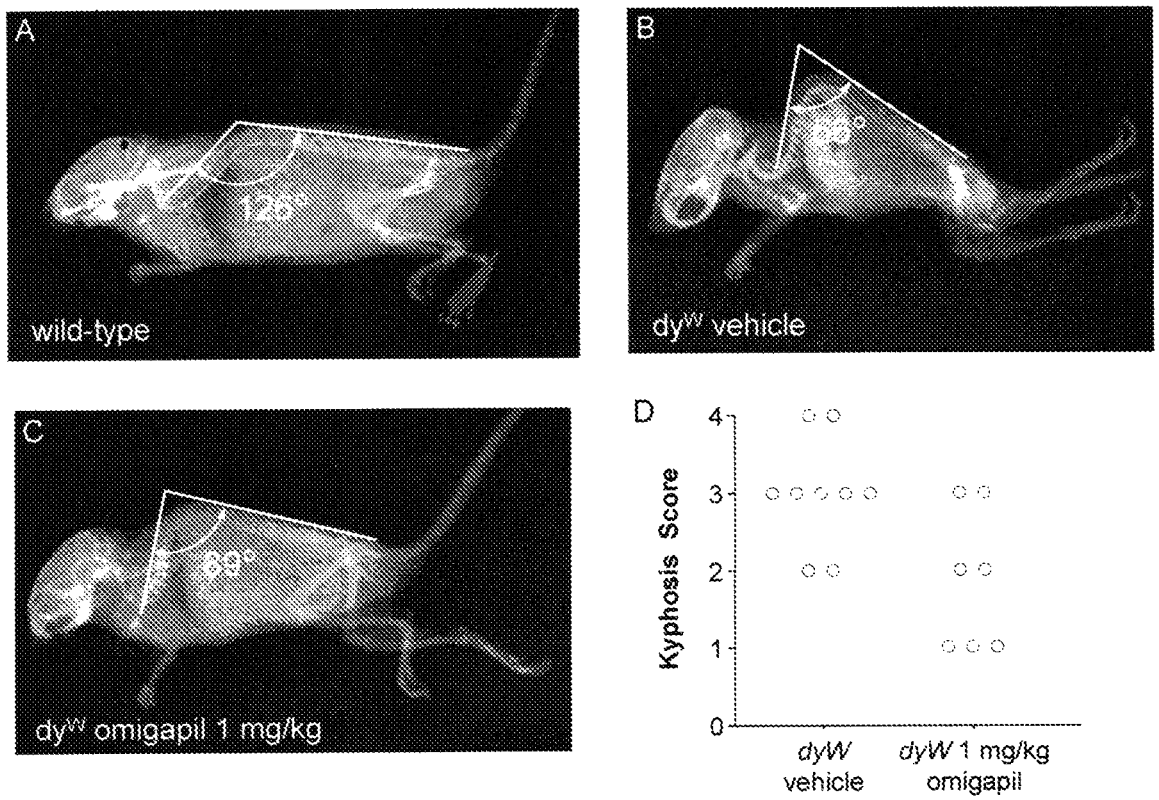
FIG. 5 (A), (B), and (C) are x-ray pictures showing kyphosis of 11-week-old mice.

FIG. 5 shows the kyphosis of 11-weeks-old dy$^W$/dy$^W$ mice. Spinal deformation was documented by X-ray pictures of an age-matched wild-type mouse (A), a vehicle-treated (B) and an 1 mg/kg omigapil-treated $dy^W/dy^W$ mouse (C). The kyphosis was quantified in living animals using a visual scoring system (1: barely detectable, 2: mild, 3: moderate, 4: severe) (D). 9 vehicle- and 7 omigapil-treated animals were analyzed.

EXAMPLE 6

The therapeutically relevant effect of N-(dibenz(b,f)oxepin-10-ylmethyl)-N-methyl-N-prop-2-ynylammonium maleate (omigapil) on the voluntary locomotion was tested in a mouse model for MDC1A deficient in laminin-α2 expression. Starting at day fifteen, homozygous $dy^W/dy^W$ mice were treated with omigapil at doses of 0.1 or 1 mg/kg body weight. Their individual exploratory locomotory activity was assessed at 6 weeks of age and compared to age-matched $dy^W/dy^W$ mice treated with vehicle only. The treatment regime was as described in example 1.

Surprisingly it was found that omigapil significantly increases the time of exploratory and voluntary locomotory activity in $dy^W/dy^W$-mice at 6 weeks of age. As demonstrated in FIG. 6, the vehicle-treated $dy^W/dy^W$ mice showed locomotory activity of 236 seconds in the 10-minute test period after placing animals in a new cage while the 0.1 and 1 mg/kg omigapil-treated groups showed locomotory activity of 330 seconds (i.e. 39% increase compared to vehicle group) and 301 seconds (i.e. 26% increase), respectively. It can be concluded that omigapil increases locomotory activity in an animal model for muscular dystrophy caused by laminin α2-deficiency.

Figure 6:
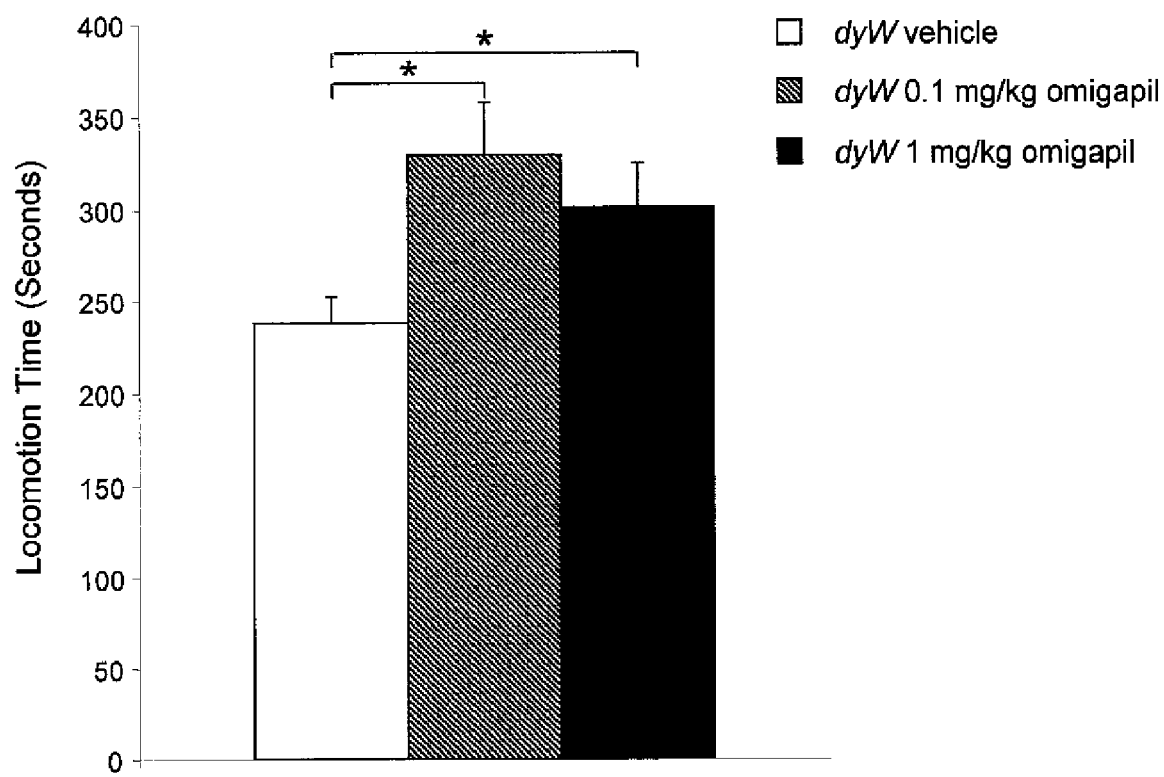
FIG. 6 is a bar graph showing the voluntary locomotory activity of 6-week-old mice.

FIG. 6 shows the time of voluntary locomotory activity of 6-weeks-old $dy^W/dy^W$ mice. Newborn $dy^W/dy^W$ mice were genotyped and randomly assigned to the vehicle or the 0.1 and 1 mg/kg omigapil groups. The voluntary locomotory activity was measured within the first 10 minutes after having placed the animal in a new cage. The vehicle-treated $dy^W/dy^W$ mice showed locomotory activity of 236 seconds while the 0.1 and 1 mg/kg body weight omigapil-treated groups showed locomotory activity of 330 and 301 seconds. The difference in activity is statistically significant for both omigapil treatments (asterisk: p-value<0.05). In total 13, 15 and 10 animals were included into the vehicle, the 0.1 and the 1 mg/kg omigapil group, respectively.

It is surprising that omigapil ameliorates several disease-specific phenotypes of laminin-α2 deficiency in a rodent model of MDC1A as determined by (1) increased body weight gain, (2) reduced apoptosis in muscle tissue, (3) normalized muscle fiber diameter, (4) reduced skeletal deformation, (5) increased locomotory activity and (6) prolonged life span. This is particularly surprising since it is not obvious to the skilled artist that inhibition of GAPDH may hold the potential to ameliorate the pathological manifestation, in particular the muscle wasting, associated with MDC1A. The apoptotic processes leading to muscle dystrophy in this disease have been attributed to the involvement of Bcl-2/Bax-pathways (Girgenrath M et al. (2004)—Inhibition of apoptosis improves outcome in a model of congenital muscular dystrophy, *J Clin Invest* 114: 1635-1639). In contrast, the involvement of GAPDH mediated cell signaling processes (Hara MR et al. (2005)—S-nitrosylated GAPDH initiates apoptotic cell death by nuclear translocation following Siah1 binding, *Nature Cell Biol* 7:665-674) have not been implicated in muscular dystrophies associated with laminin-α2 deficiency and there is currently ho evidence that Bcl-2/Bax signaling pathways and GAPDH interact in muscle diseases in general and MDC1A in particular.

The invention claimed is:

1. A method for the treatment of muscular dystrophy comprising administering to a mammal in need thereof a composition comprising a compound of formula (I)

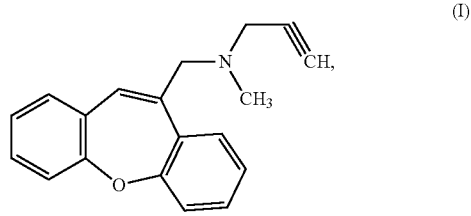

(I)

or a pharmaceutically acceptable addition salt thereof, wherein the muscular dystrophy is a congenital muscular dystrophy resulting from partial or complete loss of laminin-α2.

2. The method according to claim 1, wherein the salt of the compound of formula (I) is a salt of a mineral acid or an organic carboxylic acid.

3. The method according to claim 2, wherein the organic carboxylic acid is an optionally hydroxylated $(C_{1-7})$alkanoic acid, an optionally hydroxylated, aminated and/or oxo-substituted $(C_{2-7})$alkane-dicarboxylic acid, an optionally hydroxylated and/or oxo-substituted $(C_{3-7})$alkane-tricarboxylic acid, an optionally hydroxylated and/or oxo-substituted $(C_{4-7})$alkene-dicarboxylic acid, optionally hydroxylated and/or oxo-substituted $(C_{4-7})$alkyne-dicarboxylic acid, an aliphatic or aromatic sulfonic acid, or an aliphatic or aromatic N-substituted sulfamic acid.

4. The method according to claim 1, wherein the salt of the compound of formula (I) contains an anion selected from the group consisting of chloride, perchlorate, bromide, iodide, nitrate, phosphate, acid phosphate, sulfate, methanesulfonate, ethanesulfonate, benzenesulfonate, p-toluenesulfonate, naphthalene-2-sulfonate, bisulfate, N-cyclohexyl-sulfamate, carbonate, formate, acetate, propionate, pivalate, glycolate, lactate, gluconate, glucuronate, ascorbate, pantothenate, oxalate, malonate, succinate, glutamate, aspartate, tartrate, bitartrate, malate, citrate, aconate, fumarate, maleate, itaconate, acetylene dicarboxylate, benzoate, salicylate, phthalate, phenylacetate, mandelate, cinnamate, p-hydroxybenzoate, 2,5-dihydroxy-benzoate, p-methoxybenzoate, hydroxy naphthoate, nicotinate, isonicotinate and saccharate.

5. The method according to claim 1, wherein the salt of the compound of formula (I) contains a cation selected from the group consisting of $H^+$, $Na^+$ and $K^+$.

6. The method according to claim 1, wherein the compound is the maleate salt of the compound of formula (I).

7. The method according to claim 1, wherein the compound of formula (I) or a pharmaceutically acceptable addition salt thereof is administered orally in the form of a tablet.

8. The method according to claim 1, wherein the compound of formula (I) or a pharmaceutically acceptable addition salt thereof is administered with a second therapeutic agent.

9. The method according to claim 8, wherein the second therapeutic agent is selected from the group consisting of glucocorticosteroids, calpain inhibitors, inhibitors of the proteasome and antiinfectives.

* * * * *